United States Patent [19]
Dobson

[11] 3,974,203
[45] Aug. 10, 1976

[54] ESTERS OF HALOGENATED ALCOHOLS

[75] Inventor: Kenneth Rowland Dobson, Epsom Downs, England

[73] Assignee: BP Chemicals International Limited, England

[22] Filed: Feb. 10, 1975

[21] Appl. No.: 548,555

Related U.S. Application Data

[62] Division of Ser. No. 387,951, Aug. 13, 1973, Pat. No. 3,890,375.

[30] Foreign Application Priority Data
Aug. 25, 1972 United Kingdom............... 39644/72

[52] U.S. Cl............................. 260/476 R; 260/469
[51] Int. Cl.$^2$.................... C07C 69/76; C07C 69/78
[58] Field of Search................. 260/476 R, 633, 469

[56] References Cited
UNITED STATES PATENTS 3,644,493   2/1972   Weygant et al................. 260/485 H

*Primary Examiner*—Jane S. Myers

[57] ABSTRACT

The present invention relates to novel halogenated derivatives of esters of linear $C_8$ alcohols and a process for the preparation of such compounds.

3 Claims, No Drawings

ESTERS OF HALOGENATED ALCOHOLS

This is a division of application Ser. No. 387,951 filed Aug. 13, 1973, now U.S. Pat. No. 3,890,375.

The present invention relates to novel halogenated derivatives of esters of linear $C_8$ alcohols.

Accordingly the present invention comprises esters of linear $C_8$ alcohols of the general formula

  (I)

or

  (II)

wherein
Z is $XCH_2.CHX$—and
$Z^1$ is —$CHX.CHX$—and
X is Cl or Br,
R is a mono- or divalent aliphatic or aromatic radical,
Y is $Z(CH_2)_3.Z^1.CH_2.O.CH$ or

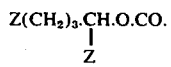

and
$x$ is 0 or 1.

Specific examples of such compounds are di(2,3,7,8-tetrachloro-1-octyl) phthalate, 2,3,7,8-tetrachloro-1-octyl acetate, 2,3,7,8-tetrachloro-1octyl propionate and 2,3,7,8-tetrachloro-1-octyl benzoate.

The carboxylic acid moiety in the ester group is derived from a saturated aliphatic or an aromatic mono- or di-carboxylic acid.

According to a further aspect of the present invention, a process for preparing compounds of the formula (I) or (II) as hereinbefore defined comprises reacting in the liquid phase an octodienyl ester with halogen at ambient temperatures.

The term "halogen" as used here and throughout the specification means chlorine or bromine.

By the term "linear $C_8$ alcohols" is meant throughout the specification that the carbon chain in the alcohol is linear. Thus the hydroxyl group of the alcohol could be in the 1- or 3- position of the carbon chain.

The octodienyl ester may suitably be prepared by reacting in the liquid phase butadiene with a carboxylic acid in the presence of a Group VIII metal catalyst as described in British Patent Specification Serial No. 1,274,072. The techniques used for this stage should be well known to a person skilled in the art.

The carboxylic acid moiety in the ester grouping is derived from a saturated aliphatic or an aromatic mono- or di-carboxylic acid. These acids may contain in addition inert substituents, e.g. halogens or alkyl groups, in the aliphatic chain or in the nuclear positions of the aromatic carboxylic acids. Suitable examples of carboxylic acids which may be used include acetic, propionic, benzoic and phthalic acids.

The product from the above esterification reaction is a mixture of 1- and 3- octadienyl mono- or di-esters depending upon whether a monocarboxylic or a dicarboxylic acid is used for the reaction.

The mixture of 1- and 3- octadienyl esters thus obtained may be used for the halogenation step after separation from the catalyst solution by liquid/liquid extraction and removal of volatile olefins by distillation. The halogenation is carried out in the liquid phase by dissolving the octadienyl esters in a solvent. The solvents used for this purpose should preferably be more volatile than the esters and be inert to halogen, e.g. a halogenated hydrocarbon such as carbon tetrachloride or chloroform. Basic solvents such as pyridine may also be present. The appropriate halogen gas, e.g. chlorine, is then passed through the solution of the octadienyl esters.

The halogenation may be carried out in the dark and/or in the presence of a free radical inhibitor such as tertiarty butyl catechol or oxygen. It may also be carried out in the presence of a Lewis acid such as ferric chloride.

The halogenation step may be carried out at ambient tempratures. By "ambient temperatures" is meant temperatures below 60°C, suitably below 40°C.

The halogenation step may be carried out at atmospheric, super-atmospheric or sub-atmospheric pressures.

The mixture of saturated halogenated derivatives thus obtained is then recovered by removal of the solvent and halogen by distillation under reduced pressure, or by liquid/liquid extraction, drying and removing the solvent by distillation.

The esters of linear $C_8$ alcohols described here may be used as plasticizers in polymeric material such as PVC, as components of lubricants and in heat exchange fluids.

The invention is further illustrated with reference to the following Examples:

EXAMPLE 1

Di(tetrachlorooctyl) phthalates

Di(octadienyl) phthalates (113g), prepared by reaction of butadiene with phthalic acid in the presence of a palladium catalyst, was dissolved in carbon tetrachloride (250 ml). The solution was cooled below 0°C by means of an ice/salt bath and cooling coil, a slow stream of oxygen was passed through the solution, and the glass reaction vessel was covered with aluminium foil to exclude light. Chlorine gas was passed into the solution at such a rate that, with cooling, the temperature did not rise above 0°C. The end of the reaction was signalled by a drop in temperature of the reaction solution. The reaction solution was washed with aqueous sodium thiosulphate solution, sodium carbonate solution, water, and dried over magnesium sulphate. Removal of the carbon tetrachloride under reduced pressure gave di(tetrachlorooctyl) phthalates (197g) as a colourless oil.

$C_{24}H_{30}O_4Cl_8$ requires: C, 43.2%; H, 4.50%; Cl, 42.6%; MW (molecular weight) 666. Found: C, 41.0%; H, 4.3%; Cl, 44.4%; MW 678.

EXAMPLE 2

2,7-octadien-1-yl acetate (16.8g; 0.10 mole) was dissolved in carbon tetrachloride (100 ml) and the solution cooled below 0°C by means of a cooling coil. A slow stream of oxygen was passed through the solution and the glass vessel covered with aluminium foil to exclude light. Chlorine was passed into the solution for 1.5 h at such a rate (90 ml. $min^{-1}$) that, with cooling, the temperature did not rise above 0°C. The reaction solution was washed with an aqueous solution of sodium sulphate/sodium bicarbonate, water (twice), and dried over magnesium sulphate. The residue remaining after removal of the carbon tetrachloride under reduced pressure was steam stripped at 70°C for 15 h and then vacuum stripped at 70°C for 6 h. The reaction product (23g) was analysed on a 1 foot × ¼ inch 5% silicone gum rubber on chromosorb W column. Three products were present in amount greater than 5 area per cent on the gas liquid chromatograph chart. The product distribution observed was:

| GC Peak | Compound | % |
|---|---|---|
| A | 1,2,3,7,8-pentachlorooctane | 17 |
| B | 1,3,7,8-tetrachloro-2-octyl acetate | 19 |
| C | 2,3,7,8-tetrachloro-1-octyl acetate | 39 |
| D | Several minor components | 25 |

1,2,3,7,8-Pentachlorooctane. Peak A was separated by solid liquid chromatography. Mass spectral analysis was consistent with the formula $C_8H_{13}Cl_5$. The nuclear magnetic resonance spectrum of 1,2,3,7,8-pentachlorooctane in $CDCl_3$ was as follows:

$$\overset{a}{CH_2Cl}\overset{b}{CHCl}\overset{c}{CH_2}\overset{d}{CH_2}\overset{e}{CH_2}\overset{f}{CHCl}\overset{g}{CHCl}\overset{h}{CH_2Cl}$$

|  | τ (tau) | Area |
|---|---|---|
| H a b f g h | 5.4 – 6.7 (m) | 7H |
| H c d e | 7.5 – 8.8 (m) | 6H |

$C_8H_{13}Cl_5$ requires: C, 33.5%; H, 4.57%; Cl, 61.9%
Found: C, 33.6%; H, 4.39%; Cl, 63.2%

1,3,7,8-tetrachloro-2-octyl acetate. Peak B was separated by solid liquid chromatography followed by preparative gas liquid chromatography. Mass spectral analysis was consistent with the formula $C_{10}H_{13}O_2Cl_4$. The nuclear magnetic resonance spectrum of 1,3,7,8-tetrachloro-2-octyl acetate appeared as follows:

$$\overset{a}{CH_2Cl}\overset{b}{CHCl}\overset{c}{CH_2}\overset{d}{CH_2}\overset{e}{CH_2}\overset{f}{CH}\overset{g}{CHCl}\overset{h}{CH_2Cl}$$
$$\qquad\qquad\qquad\qquad\;\;|\\ \qquad\qquad\qquad\qquad OCOCH_3\;(i)$$

|  | τ (tau) | Area |
|---|---|---|
| H g | 4.85 (m) | 1H |
| H a b f h | 5.6 – 6.6 (m) | 6H |
| H i | 7.87 (S) | 3H |
| H c d e | 7.9 – 8.8 (m) | 6H |

Proton decoupling at 8.22 τ (tau) resulted in no simplification of the 4.85 multiplet.

$C_{10}H_{13}O_2Cl_4$ requires: C, 38.7%; H, 5.20%; Cl, 45.7% found: C, 37.3%; H, 5.06%; Cl, 47.7%

2,3,7,8-tetrachloro-1-octyl acetate. Peak C was separated by solid liquid chromatography followed by preparative gas liquid chromatography. Mass spectral analysis was consistent with the formula $C_{10}H_{13}O_2Cl_4$. The nuclear magnetic resonance spectrum of 2,3,7,8-tetrachloro-1-octyl acetate in $CDCl_3$ was as follows:

$$\overset{a}{CH_2Cl}\overset{b}{CHCl}\overset{c}{CH_2}\overset{7.7\;d}{CH_2}\overset{e}{CH_2}\overset{f}{CHCl}\overset{g}{CHCl}\overset{h}{CH_2}\overset{i}{OCOCH_3}$$

|  | τ (tau) | Area |
|---|---|---|
| H h | 5.5 (m) | 2H |
| H a b f g | 5.5 – 6.6 (m) | 5H |
| H i | 7.89 (s) | 3H |
| H c d e | 7.1 – 8.8 (m) | 6H |

$C_{10}H_{13}O_2Cl_4$ requires: C, 38.7%; H, 5.20%; Cl, 45.7%; MW, 310 found: C, 38.7%; H, 4.99%; Cl, 46.8%; Mol Wt 325

As can be seen from this Example, the process also results in the formation of the 2-ester besides the 1- and/or 3- esters.

EXAMPLE 3

1,7-Octadien-3-yl acetate (168g; 0.10 mole) in carbon tetrachloride (150 ml) was treated with chlorine as described in example 2 except that the chlorine was passed at 50 ml min⁻¹ for 3h. The reaction product (26.4 g) was isolated and analysed by gas liquid chromatography as described in Example 2. Three products were present in amounts greater than 5 area percent:

| GC Peak | Compound | % |
|---|---|---|
| A | 1,2,3,7,8-pentachlorooctane | 33 |
| B | 1,2,7,8-tetrachloro-3-octyl acetate | 55 |
| C | unidentified | 11 |

1,2,3,7,8-Pentachlorooctane. Peak A was separated by solid liquid chromatography. Identification was based on a comparison of its mass spectrum and its nuclear magnetic resonance spectrum with those of 1,2,3,7,8-pentachlorooctane from Example 2. They also had the same gas liquid chromatograph retention times.

1,2,7,8-tetrachloro-3-octyl acetate. Peak B was separated by solid liquid chromatography. Mass spectral analysis was consistent with the formula $C_{10}H_{13}O_2Cl_4$. The nuclear magnetic resonance spectrum of 1,2,7,8-tetrachloro-3-octyl acetate was as follows:

$$\overset{a}{CH_2Cl}\overset{b}{CHCl}\overset{c}{CH_2}\overset{d}{CH_2}\overset{e}{CH}\overset{f}{CH_2}\overset{g}{CHCl}\overset{h}{CH_2Cl}$$
$$\qquad\qquad\qquad\qquad\;\;|\\ \qquad\qquad\qquad\qquad OCOCH_3$$

|  | τ(tau) | Area |
|---|---|---|
| H f | 4.75 (m) | 1H |
| H a b g h | 5.6 – 6.7 (m) | 6H |
| H i | 7.88 (s) | 3H |
| H c d e | 7.7 – 8.8 (br) | 6H |

Proton decoupling at 8.22 τ (tau) simplified the 4.75 multiplet to a double-doublet.

$C_{10}H_{13}O_2Cl_4$ requires: C, 38.7%; H, 5.20%; Cl, 45.7% found: C, 38.9%; H, 5.13%; Cl, 45.4%

EXAMPLE 4

2,7Octadien-1-yl acetate (6.7g; 0.04 mole) was dissolved in chloroform (36 ml) containing pyridine (4 ml) and then treated with chlorine at 40 ml min⁻¹ for 57 min in the same manner as described in Example 2 except that the temperature was kept below −15°C. The reaction solution was diluted with chloroform (100 ml), washed with water, and dried over magnesium sulphate. The chloroform was removed under reduced pressure and the residue stripped as in Example 2. GLC analysis indicated that the product (10.8 g) contained 2,3,7,8-tetrachloro-1-octyl acetate (95%).

EXAMPLE 5

Tetrachlorooctyl propionates

Octadienyl propionates (91g), prepared by the reaction of butadiene with propionic acid in the presence of a palladium catalyst, were dissolved in carbon tetrachloride (200 ml). The solution was treated with chlorine and the product isolated as described in Example 1. Tetrachlorooctyl propionates (154g) were obtained as an oil.

$C_{11}H_{18}O_2Cl_4$ requires: C, 38.7%; H, 5.2%; Cl, 45.8%; MW 310 found: C, 37.2%; H, 4.7%; Cl, 46.9%; MW 333

EXAMPLE 6

2,7-Octadien-1-yl benzoate (92.4g; 0.4 mole) was dissolved in chloroform (270 ml) and pyridine (30ml) and then treated with chlorine at 90 ml min$^{-1}$ for 3.7$h$ in the same manner as described in Example 2 except that the temperature was kept below −5°C. The reaction solution was diluted with chloroform (270 ml), washed with water, dilute hydrochloric acid (2×), sodium carbonate solution, water, and dried over magnesium sulphate. Removal of the chloroform under reduced pressure gave a dark brown oil (123g). The reaction product was decolourised by passing a solution in benzene/hexane (1:1) down a column of activated charcoal. Removal of benzene/hexane from the eluate gave a pale yellow oil, which was steam stripped at 80°C. for 6$h$ and vacuum stripped at 80°C for 6$h$. GLC analysis indicated that the product (89g) contained 2,3,7,8-tetrachloro-1-octyl benzoate (77%).

I claim:
1. An ester of the general formula:

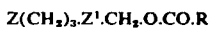

or

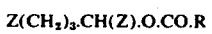

wherein
 Z is XCH$_2$.CHX—,
 Z$^1$ is —CHX.CHX—,
 X is Cl or Br, and
 R is a monovalent aromatic hydrocarbn radical which may be substituted by halogen or alkyl.
2. The ester of claim 1, wherein R is phenyl.
3. 2,3,7,8-tetrachloro-1-octyl benzoate.

* * * * *